United States Patent [19]

Reed

[11] Patent Number: 4,919,534

[45] Date of Patent: Apr. 24, 1990

[54] SENSING OF MATERIAL OF CONSTRUCTION AND COLOR OF CONTAINERS

[75] Inventor: Michael A. Reed, Greenland, N.H.

[73] Assignee: Environmental Products Corp., Del.

[21] Appl. No.: 251,559

[22] Filed: Sep. 30, 1988

[51] Int. Cl.$^5$ .................. G01J 3/50; G01N 21/21; G01N 21/27

[52] U.S. Cl. ..................... 356/73; 250/223 B; 250/225; 250/226; 356/367; 356/402; 356/407; 356/425; 209/524; 209/582

[58] Field of Search ............... 356/73, 364, 366, 367, 356/402, 406, 407, 416, 419, 425, 428; 250/223 B, 225, 226; 209/524, 580–582, 588

[56] References Cited

U.S. PATENT DOCUMENTS

| | | |
|---|---|---|
| 2,332,308 | 10/1943 | Dresser . |
| 3,421,820 | 1/1969 | Huebschman . |
| 3,639,771 | 2/1972 | Borelli et al. .................. 250/225 |
| 3,724,952 | 3/1973 | Vossberg ...................... 250/225 |
| 3,963,348 | 6/1976 | Nakatani et al. ............... 356/33 |
| 4,017,194 | 4/1977 | Conroy ......................... 356/240 |
| 4,076,979 | 2/1978 | Walter et al. ................. 250/226 |
| 4,141,493 | 2/1979 | Arp . |
| 4,248,334 | 2/1981 | Hanley et al. . |
| 4,248,389 | 2/1981 | Thompson et al. . |
| 4,285,426 | 8/1981 | Cahill . |
| 4,547,067 | 10/1985 | Watanabe ...................... 356/239 |
| 4,589,776 | 5/1986 | Carver et al. ................. 250/225 |

FOREIGN PATENT DOCUMENTS

3445428  6/1986  Fed. Rep. of Germany ...... 209/524

Primary Examiner—F. L. Evans
Attorney, Agent, or Firm—Finnegan, Henderson, Farabow, Garrett & Dunner

[57] ABSTRACT

An apparatus and process permit the material of construction and the color of transparent and partly transparent containers to be determined rapidly and accurately. To determine the material of construction, polarized light is passed through the container, portions of the transmitted beam are analyzed by parallel and cross polarizers, the intensities of the analyzed beams are measured, and the sum and difference of the analyzed beams are determined. Preferably, the determination is made with at least two wavelengths of polarized light, and the sums and differences of the intensities of the different wavelengths are determined. Glass containers do not alter the polarization of the transmitted light, while many types of plastic containers do alter the polarization, and this difference serves as the basis for the differentiation. The color of the container, whether it be glass or plastic, is determined by calculating a color index as the difference in the transmitted intensity for light of different wavelengths, and this difference, particularly when normalized by the sum of the transmitted intensities, serves as a color index for characterizing the color of the container. An automated apparatus for performing this determination is provided.

17 Claims, 6 Drawing Sheets

SENSING OF MATERIAL OF CONSTRUCTION AND COLOR OF CONTAINERS

BACKGROUND OF THE INVENTION

This invention relates to the characterization of containers, and, more particularly, to a process and apparatus for determining the material of construction and the color of transparent and partially transparent containers.

In recent years, non-deposit containers for beverages and other goods have become widely used because their cost has been less than the cost of recycling and/or cleaning for reuse, previously used deposit containers and bottles. One significant result of the widespread use of non-deposit containers has been increased litter in public places.

To combat litter and increase the amount of material that is recycled, several states have now enacted mandatory "deposit laws" that require the use of containers having a deposit thereon. When the customer purchases a product in such a container, a container deposit, typically one to five cents, is added to the purchase price. After consumption of the product, the consumer can obtain a refund of the deposit by returning the empty container for recycling. The amount of the deposit may be adjusted to create an incentive for returning the container that is greater than the inconvenience in doing so.

For the recycling system to work properly, the scrap sales value of the recycled material must be sufficiently greater than the cost of recycling so that the recycling activity is profitable. Some candidates for recycling, such as aluminum, have an inherently high scrap value, and there has been widespread industry acceptance for recycling. Other scrap materials, for example glass and plastics such as polyethylene terephthalate (PET), have such a low scrap value that it is difficult for the value of the recycled material to exceed the costs of recycling.

One approach to improving the economics of recycling is to reduce the costs of recycling, particularly the labor cost of receiving containers and passing out the proper refund. Some groups and individuals, such as retailers, have opposed mandatory deposit laws because, they argued, the high labor cost of processing recycled material makes recycling uneconomic, particularly for low scrap value materials, such as glass and PET. To reduce the labor cost, various automatic machines that accept material for recycling and issue deposit refunds have been proposed, and some have been placed into service. Such machines do achieve their objective of reduced labor cost.

Another approach to improving the economics of recycling is to increase the scrap value of the recycled material. One method for increasing the scrap value is to segregate the returned material into groups whose scrap price is inherently higher than is unsegregated material. For example, the value of glass and PET, per pound, is greater when the two have been segregated than when they are mixed together. Carrying the example further, the value of glass (or PET) that has been segregated by color (for example, clear, red, or green) is greater than the value of glass that is mixed together.

In the past, the segregation of returned containers into classes has been labor intensive, so that the labor to perform the sorting may cost more than the increase in resale value of the segregated material. It would be highly desirable to provide a device that can perform the separation of materials into such groups quickly and inexpensively, so that the cost of the sorting process is less than the enhancement in value obtained through sorting. It would be particularly desirable to provide such a sorting device that could be utilized at the point of return of the recycled material, because the person charged with recycling (typically the retainer) would enjoy the enhancement in profit arising from its use. It is expected that such an approach would greatly increase industry support for recycling glass and PET.

There is presently available no apparatus and process for grading and sorting returned glass and PET by material of construction and color. Such a device should meet the requirements discussed previously, and also be operable with containers that are less than ideal, such as those which are dirty or have labels. The present invention fulfills this need, and further provides related advantages.

SUMMARY OF THE INVENTION

The present invention provides an apparatus and process for sorting returned containers automatically, that is, without the intervention or participation of a human being. Containers that are transparent or partially transparent may be sorted as between optically active and optically inactive materials, and as between different colors. Optically active materials are those that cause the rotation of polarized light. Some plastics, most commonly polyethylene terephthalate (PET) in the container industry, are optically active. Glass such as used in containers is typically optically inactive. Thus, the present approach gives an inexpensive, reliable method of sorting glass containers from PET containers, and any type of transparent or partially transparent container by color. The sorting is accomplished rapidly, normally as fast as a customer can place the containers into the apparatus. Once sorted, the recycled materials are conveyed to appropriate bins of like-type materials.

In accordance with the invention, apparatus for recycling glass and plastic containers provided by a customer comprises means for receiving a container from a customer; means for providing to the customer a reward for providing the container; and means for automatically sorting the container by material of construction, as between glass and an optically active material, and for sorting the container by color.

It has been previously known to provide a device that can receive containers and provide a reward to the customer, in the form of cash or coupons. However, no means for automatically performing the sorting has been known, where "automatic" as used herein means without human intervention or assistance.

Further in accordance with the invention, apparatus for analyzing the character of a light transmitting container comprises a container support adapted for supporting a container; a first source of a beam of polarized light of a first wavelength disposed to direct the beam of polarized light through the container supported in the container support; a second source of a beam of polarized light of a second wavelength disposed to direct the beam of polarized light through the container supported in the container support; a first light analyzer having a parallel polarizer relative to the polarization of the light from the first source, the parallel polarizer being disposed to intercept a first portion of the beam from the first source of polarized light after the beam has passed through the container, a cross polarizer relative to the polarization of the light from the first source, the cross polarizer being disposed to intercept a second portion of the beam from the first source of polarized light after the beam has passed through the container, a first detector that measures the intensity of a light beam, the first detector being disposed to detect the first portion of the beam from the first source, after the beam has passed through the parallel polarizer, and a second detector that measures the intensity of a light beam, the second detector being disposed to detect the second portion of the beam from the first source, after the beam has passed through the cross polarizer; a second light analyzer having a parallel polarizer relative to the polarization of the light from the second source, the parallel polarizer being disposed to intercept a first portion of the beam from the second source of polarized light after the beam has passed through the container, a cross polarizer relative to the polarization of the light from the second source, the cross polarizer being disposed to intercept a second portion of the beam from the second source of polarized light after the beam has passed through the container, a first detector that measures the intensity of a light beam, the first detector being disposed to detect the first portion of the beam from the second source, after the beam has passed through the parallel polarizer, and a second detector that measures the intensity of a light beam, the second detector being disposed to detect the second portion of the beam from the second source, after the beam has passed through the cross polarizer; and means for analyzing the character of the container using the intensities measured by the first light analyzer and the second light analyzer.

Preferably, the means for analyzing may include means for determining the sum of the intensities measured by the first detector of the first light analyzer and the first detector of the second light analyzer. It also desirably includes means for determining the difference of the intensities measured by the first detector of the first light analyzer and the first detector of the second light analyzer, as a measure of the color of the container.

In this embodiment, the apparatus directs beams of polarized light of different colors through the container. Part of each transmitted beam is passed through a parallel polarizer, and part through a crossed polarizer. The intensity of the various beams is measured. The different between the intensities for the parallel polarized beams of different colors, or the cross polarized beams of different colors, is a color index that is a measure of the color of the beam.

In a more preferred embodiment of the invention, the beams of the two light sources are made coincident, and the beams from the two sources are alternatingly directed through the container. Ambient light conditions are determined in the periods when neither light source is operating. In accordance with this aspect of the invention, apparatus for analyzing the character of a light transmitting container comprises a container support adapted for supporting a container; a first source of a beam of light of a first wavelength disposed to direct the beam of light through the container supported in the container support; a second source of a beam of light of a second wavelength disposed to direct the beam of light through the container supported in the container support, the first source and the second source being disposed so that the beam of light of the first wavelength and the beam of light of the second wavelength are at least in part parallel and coincident on a beam path; a first polarizer disposed in the beam path at a location prior to passage of the beams through the container; a beam controller that controls the operation of the first light source and the second light source to operate in an alternating fashion; a light analyzer having a parallel polarizer relative to the polarization of the light from the first polarizer, the parallel polarizer being disposed to intercept a first portion of the beam path at a location after the beams have passed through the container, a cross polarizer relative to the polarization of the light from the first polarizer, the cross polarizer being disposed to intercept a second portion of the beam path at a location after the beams have passed through the container, a first detector that measures the intensity of a light beam, the first detector being disposed to detect the light passing through the parallel polarizer, and a second detector that measures the intensity of a light beam, the second detector being disposed to detect the light passing through the cross polarizer; and means for analyzing the character of the container using the intensities measured by the light analyzer.

In this preferred embodiment, the apparatus includes a trough or pair of rails upon which the container is supported, typically such that the container slides past a measurement station. Light beams from light sources operating at different wavelengths are polarized and directed through the container in an alternating sequential fashions, with periods of illumination separated with periods where no illumination is provided. The beams are superimposed along a common optical axis. Preferably, the light sources are light emitting diodes emitting in the red (nominally 6650 Angstroms) and green (nominally 5600 Angstroms) ranges. Thus, the beam is composed of a periodically repeating light signal, the first portion having a first wavelength, the second portion having a second wavelength, and the third portion being ambient light only.

A portion of the transmitted beam is passed through a first analyzing polarizer whose polarization axis is parallel to that of the initial polarizer. A second portion of the transmitted beam is passed through a second analyzing polarizer whose polarization axis is crossed with respect to that of the initial polarizer. The first and second portions of the transmitted beam are each focused onto a photodetector, such as a photodiode, that produces an output signal responsive to the intensity of the light. The intensity of the received light is integrated over the period of receipt, yielding a total integrated intensity for each beam, and a total integrated intensity of ambient light received by each detector. The true intensity of each beam signal is obtained by subtracting the average ambient light signal from the beam signal, thus obtaining an accurate measure of light intensity of each beam for each of its periods of illumination.

This information is used to sort the container by material of construction and by color. As a first step, a total transmitted energy for both wavelengths is obtained, for each of the two beams (parallel and crossed polarizers), and a difference in transmitted energy for the two wavelengths is obtained, for each of the two beams. The difference is also termed the color index, for reasons that will become apparent. A normalized color index (NCI) is calculated as the quotient obtained by dividing the color index by the total transmitted energy for each beam.

For a glass container, the total energy for both of the beams, passing through the parallel and crossed polarizers, respectively, will decrease as compared with the total transmitted energy determined when no container is present. For an optically active material such as PET or other optically active plastics, the energy of the beam passing through the parallel polarizer decreases as compared with the cross polarized energy due to the rotation of the polarized beam by the optically active material. A microprocessor in the apparatus performs this logical analysis, and signals the material of construction.

The color of the container is obtained from the normalized color index calculated for either the parallel or crossed polarization beams. Normally, both are determined for verification purposes. Where the color of the container is about that of the color of the beam emitted from the first light source, the normalized color index is positive, because the light of the first light source is transmitted with little attenuation and light of the second light source is highly attenuated. Where the color of the container is about that of the color of the beam emitted from the second light source, the normalized color index is negative, because the light of the first light source is highly attenuated and the light of the second light source is transmitted with little attenuation. Where the container is clear, the normalized color index is near zero, because both wavelengths are transmitted equally. The microprocessor performs this logical analysis, and signals the color of the container.

A mechanical sorter utilizes the logical signals from the microprocessor to sort the containers as between glass and optically active material, and as between colors. This sorting is performed at the machine and without the need for hand sorting or human intervention of any kind.

The principle of color analysis can be extended to multiple light sources of differing wavelengths. However, it has been found from practical experience that, for most scrap processing requirements, sorting as between red, green, and clear material is sufficient. For containers of other colors, a quantitative criterion may be provided to the microprocessor so that each container is sorted to its closest match. Alternatively, containers of other colors could be sorted to a bin for return to the customer if such colors are unacceptable.

It is apparent, of course, that the analyses of material of construction and color of container are independent of each other, and in some circumstances only one or the other type of sorting may be provided. In accordance with the invention, apparatus for determining whether a container is formed of glass or an optically active plastic comprises a container support adapted for supporting a container of an unknown, but optically transmissive material; a source of a beam of light disposed to direct the beam of light through the container supported in the container support; a first polarizer disposed in the beam path at a location prior to passage of the beam through the container; a light analyzer having a parallel polarizer relative to the polarization of the light from the first polarizer, the parallel polarizer being disposed to intercept a first portion of the beam at a location after the beam has passed through the container, a cross polarizer relative to the polarization of the light from the first polarizer, the cross polarizer being disposed to intercept a second portion of the beam at a location after the beam has passed through the container, a first detector that measures the intensity of a light beam, the first detector being disposed to detect the light passing through the parallel polarizer, and a second detector that measures the intensity of a light beam, the second detector being disposed to detect the light passing through the cross polarizer; and means for determining the difference of the intensity measured by the first detector and the intensity measured by the second detector.

Also in accordance with the invention, apparatus for determining the color of a container that is transmissive to light comprises a container support adapted for supporting a container; a first source of a beam of light of a first wavelength disposed to direct the beam of light through the container supported in the container support; a second source of a beam of light of a second wavelength disposed to direct the beam of light through the container supported in the container support; a first light analyzer having a first detector that measures the intensity of a light beam, the first detector being disposed to detect the intensity of the beam from the first source, after the beam has passed through the container, and a second detector that measures the intensity of a light beam, the second detector being disposed to detect the intensity of the beam from the second source, after the beam has passed through the container; and means for determining the difference of the intensities measured by the first detector and the second detector.

The present invention also extends to processes for performing the determination of material of construction and color of containers, either in conjunction with, or independent of, the apparatus previously described. In such processes, the principles of operation are as described. In accordance with the invention, a process for determining whether a container is formed of glass or an optically active plastic comprises the steps of finding a polarization difference index for the container, utilizing the steps of passing a beam of polarized light through a container, passing a portion of the beam through a parallel polarizer, after it has passed through the container, passing another portion of the beam through a cross polarizer, after it has passed through the container, and determining the polarization difference index as the difference in intensity of the portion of the beam passed through the parallel polarizer and the intensity of the portion of the beam passed through the cross polarizer; repeating the step of finding with no container present; and comparing the polarization difference index determined with a container present and with no container present.

Also in accordance with the invention, a process for determining the color components of a container that is at least partly transparent to light, comprising the steps of transmitting a beam of light through the container, the beam having at least two different wavelengths therein; measuring the intensity of the transmitted beam at the two different wavelengths; and calculating a color index of the container as the difference between the intensities of the beam at the two different wavelengths.

Further in accordance with the invention, a process for characterizing the nature of a container that is at least partially transparent to light, comprising the steps of transmitting a beam of light through the container, the beam having at least two different wavelengths therein; measuring the intensity of the transmitted beam at the two different wavelengths; calculating a color index of the container as the difference between the intensities of the beam at the two different wavelengths; finding a polarization difference index for the container, utilizing the steps of passing a beam of polarized light through a container, passing a portion of the beam through a parallel polarizer, after it has passed through the container, passing another portion of the beam through a cross polarizer, after it has passed through the container, and determining the polarization difference index as the difference in intensity of the portion of the beam passed through the parallel polarizer and the intensity of the portion of the beam passed through the cross polarizer; repeating the step of finding with no container present; and comparing the polarization difference index determined with a container present and with no container present.

Thus, the apparatus and process of the invention provide an approach for accomplishing the sorting of containers that are at least partially transparent to light, without the use of human labor or intervention. The approach is operable in conjunction with a recycling machine or the like, so that the customer is rewarded for recycling the material with a cash refund or coupons that may be redeemed. Other features and advantages of the present invention will be apparent from the following more detailed description of the invention, taken in conjunctions with the accompanying drawings, which illustrate, by way of example, the principles of the invention.

DETAILED DESCRIPTION OF THE PREFERRED EMBODIMENT

Figure 1:
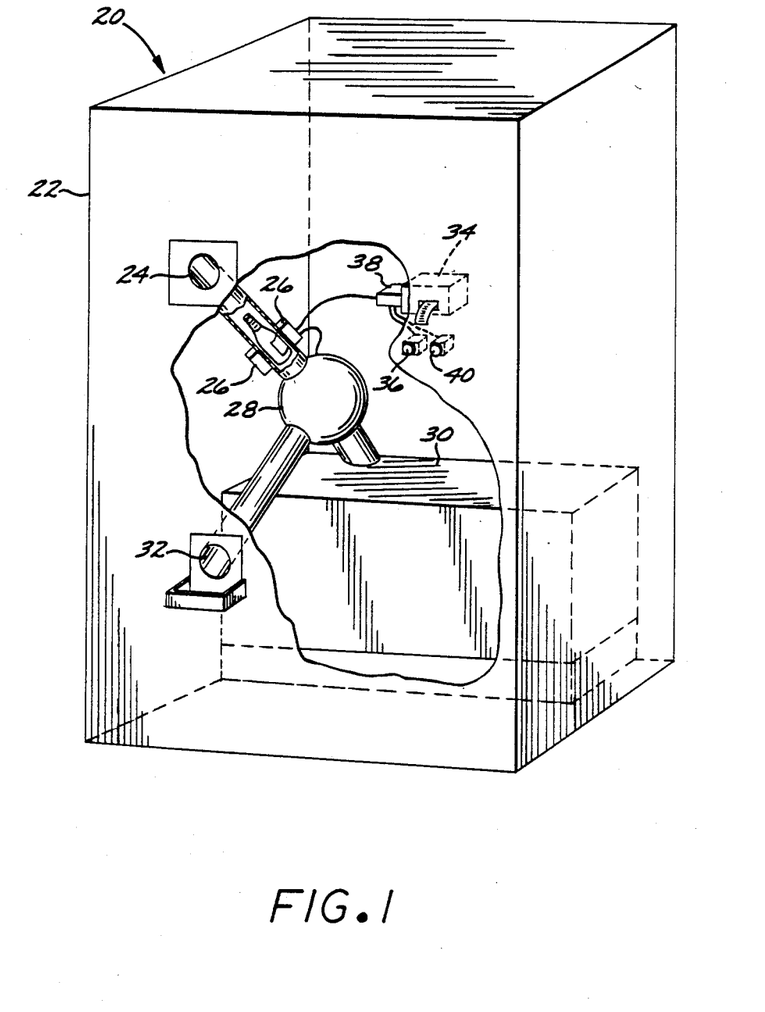
FIG. 1 is a perspective view of a recycling apparatus employing the apparatus and process of the invention, with interior portions illustrated in cut away view for clarity.

As illustrated in FIG. 1, the present invention includes recycling apparatus 20 for receiving and sorting containers. The apparatus 20 includes a housing 22 having a receiving receptacle 24 therein, for receiving empty containers inserted therein by a customer. Containers received in the receptacle 24 are passed through a sorting station 26, whose operation is described in greater detail below. Sorted containers leave the sorting station 26 travel through a sorting gate 28, and into one of a plurality of bins 30 for storage and/or crushing, or to a return chute 32 that returns unacceptable containers to the customer. The sorting gate 28 directs the container to the proper bin 30 for storage or crushing, or the return chute 32 under command of the sorting station 26.

A reward dispenser 34 delivers to the customer a reward for returning the containers, typically in the form of cash or coupons redeemable for goods, under control of a reward total accumulator 38. On the face of the apparatus 20 is a start button 36 that signals the apparatus 20 that a particular customer is commencing the return of a series of one or more containers. Depressing the start button 36 causes the reward accumulator 38 to be set to zero. Each acceptable container sensed by the sorting apparatus 26 causes the reward accumulator 38 to be incremented the proper amount, thereby keeping a running total of the reward due the customer. When the customer has deposited all the containers to be returned, an end button 40 is depressed to signal the reward accumulator 38 that the return process is completed. The reward accumulator 38 signals the total reward to the reward dispenser 34, which then delivers the reward to the customer. The reward dispenser typically permits the customer to choose whether the reward is to be in the form of cash or other type of available reward. The structure of the recycling apparatus is known to those skilled in the art, except for the operation of the sorting apparatus or station 26, and is described, for example, in U.S. Pat. Nos. 4,248,389 and 4,248,334, whose disclosures are incorporated by reference.

Figure 6:
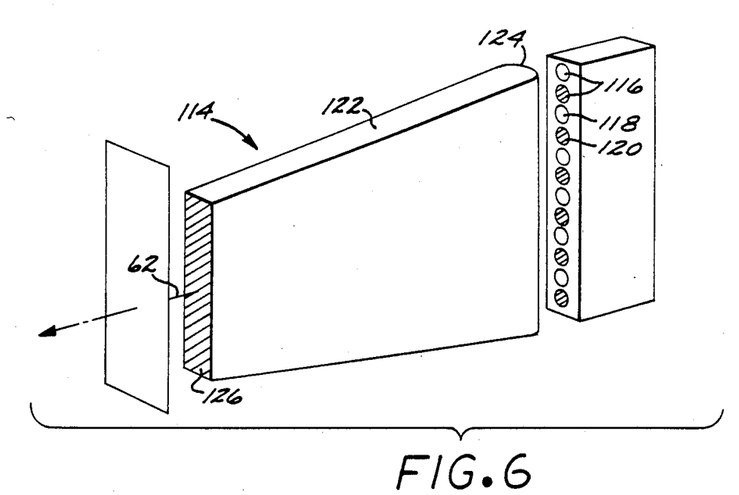
FIG. 6 is a perspective view of another embodiment of a light source.
Figure 7:
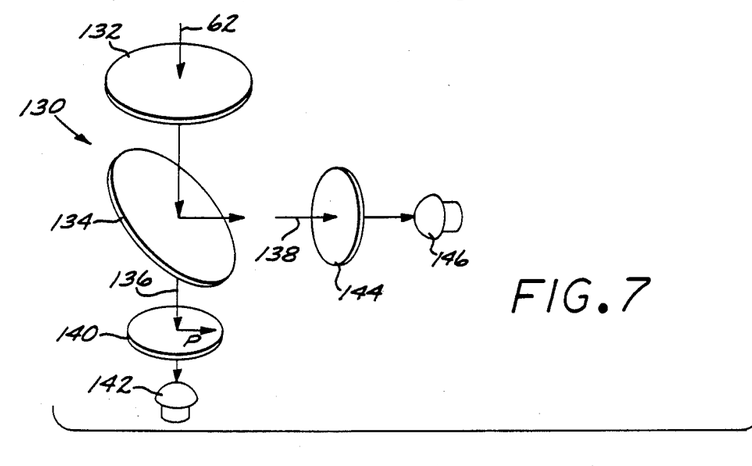
FIG. 7 is a perspective view of the internal elements of the coaxial light analyzer depicted in FIG. 5.
Figure 8:
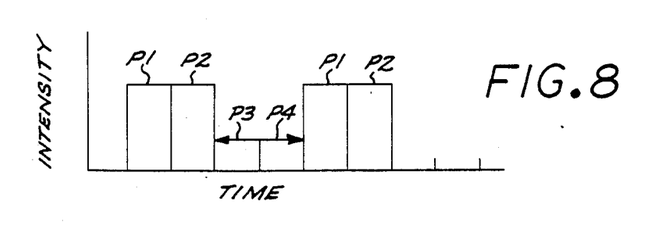
FIG. 8 is a timing diagram for the operation of the light sources.
Figure 9:
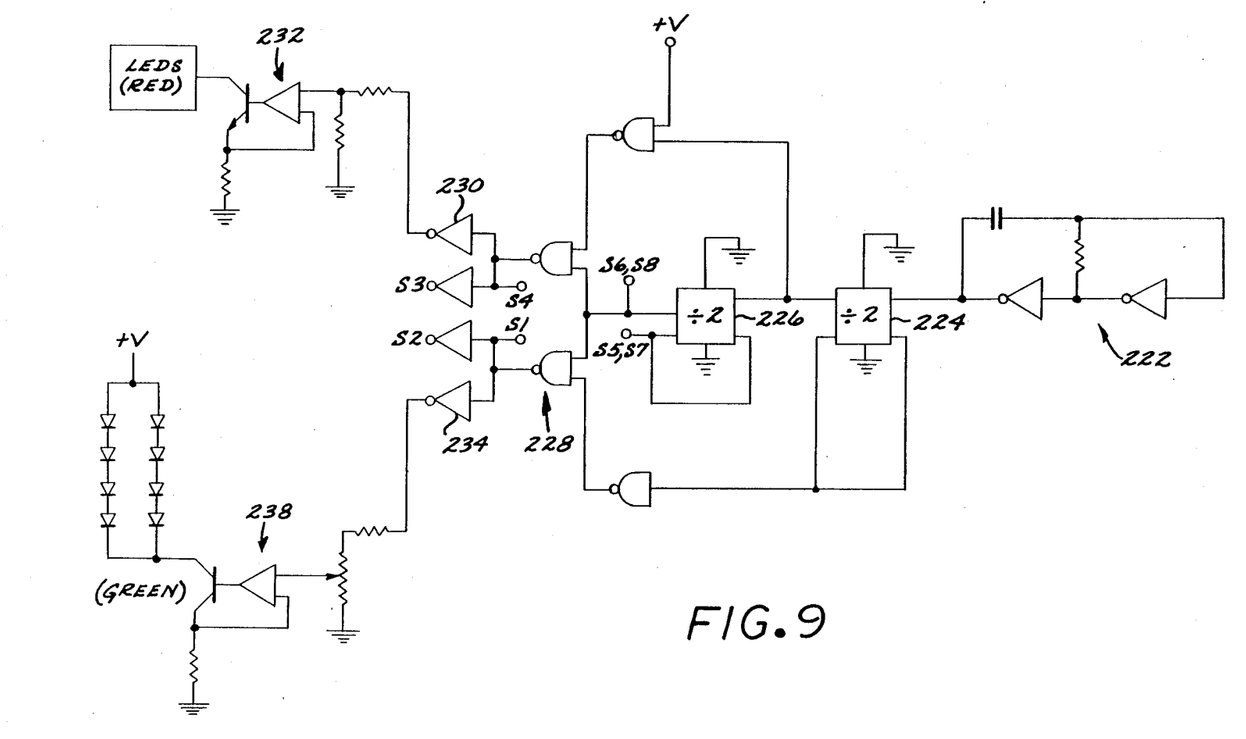
FIG. 9 is an electronic circuit diagram for the operation of the light sources.
Figure 10:
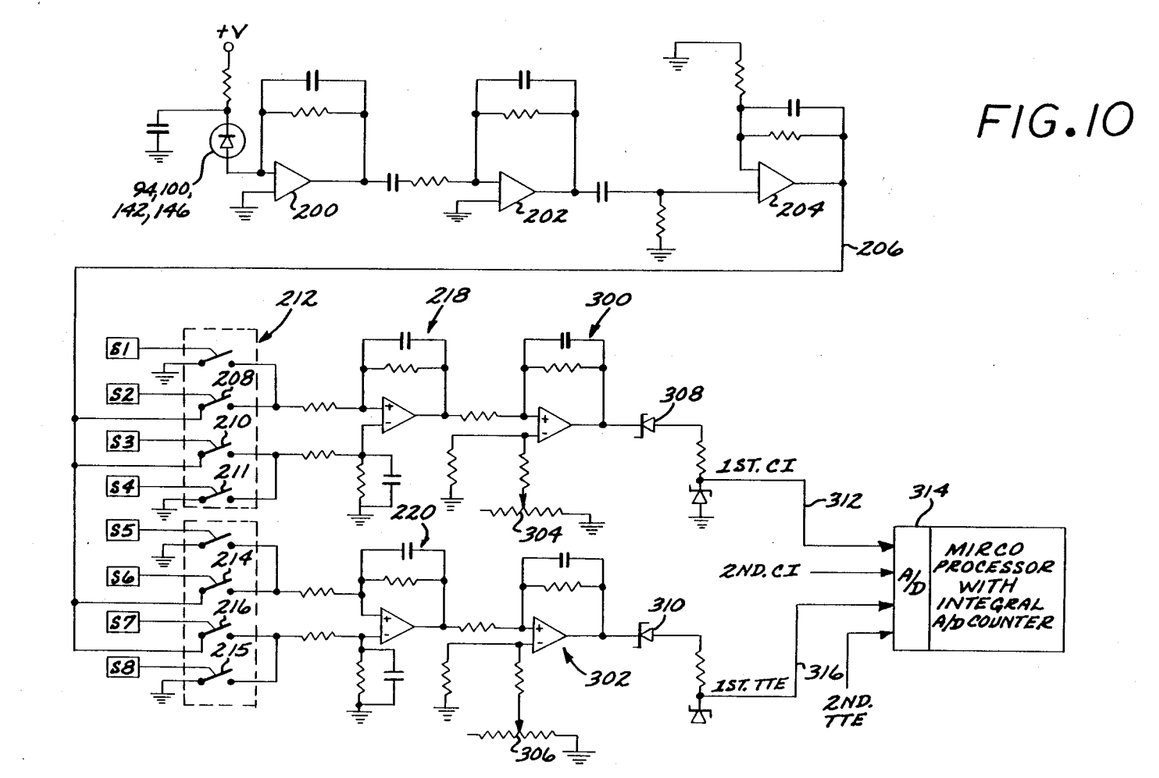
FIG. 10 is an electronic circuit diagram for the processing of the analyzer signals.

FIGS. 2-4 and 5-7 illustrate two preferred physical embodiments of the sorting apparatus, FIG. 8 is a timing diagram for the operation of the light sources in the physical embodiments, and FIGS. 9 and 10 present preferred forms of the electronic circuits used in the sorting apparatus.

Figure 2:
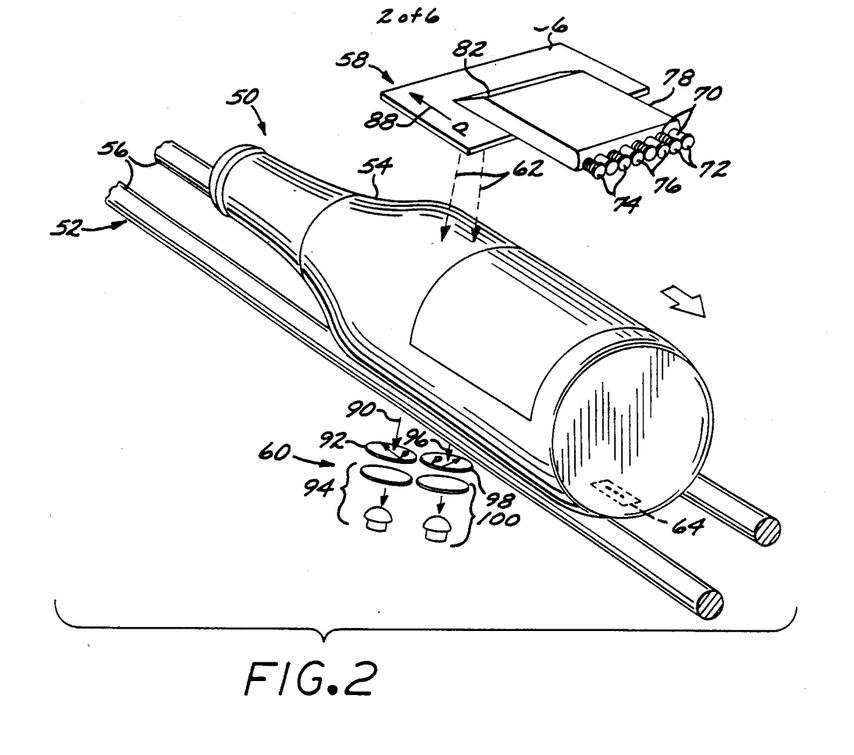
FIG. 2 is a perspective diagrammatic view of a container measurement apparatus utilizing the approach of the invention.
Figure 3:
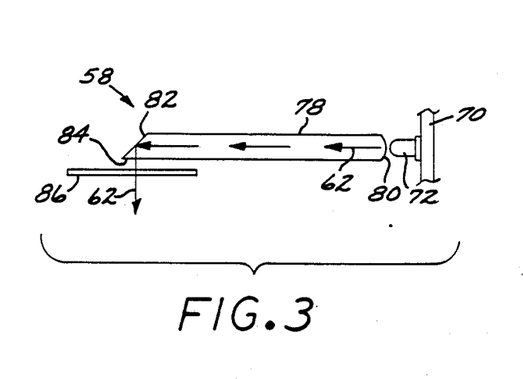
FIG. 3 is a side view of the light source of FIG. 2.
Figure 4:
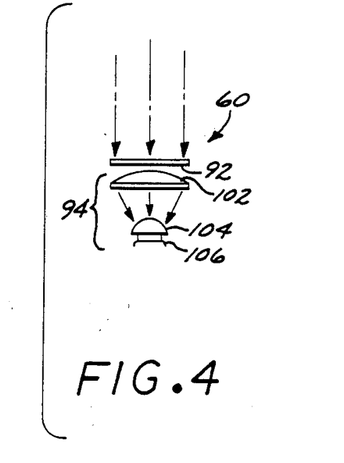
FIG. 4 is a side view of the light analyzer of FIG. 2.

Referring first to FIGS. 2-4, a sorting station 50 includes a support 52 for a container 54, the support 54 typically being in the form of a pair of rails 56 along which the container slides. The container 54 moves past a light source assembly 58 and an oppositely disposed light analyzer assembly 60. The assemblies 58 and 60 are positioned so that a light beam 62 from the light source assembly 58 passes through the container 54 and is received by the light analyzer assembly 60. Typically, the surface of the container may be partially covered by an opaque covering such as a paper label or bar code, and the apparatus is constructed and operated so that it is operable as long as the light beam 62 is able to penetrate through at least some portion of the container. A trip switch 64 is positioned to be operated when the container 54 is in position so that the light beam 62 from the source assembly 58 to the analyzer assembly 60 passes through the container 54, signalling that a container 54 is in place for a sensing and sorting measurement.

In the preferred embodiment, both the material of construction of the container and the color of the container are sensed, and the information is utilized in the sorting process. It is understood that the apparatus could be constructed so that only the material of construction or the color of the container would be sensed, as described previously.

The light source assembly 58 is illustrated in FIGS. 2 and 3. The assembly 58 includes a light emitter 70, that includes sources of at least two different wavelengths of light and produces a line source of light. In the preferred approach, the light emitter 70 includes four pairs of light emitting diodes 72 arranged linearly in a row and facing the same direction. The pairs are arranged in alternating fashion, so that every other diode produces light of the same wavelength. In the preferred approach, one set of diodes 74 produces red light having a wavelength of about 6650 Angstroms, and the other set of diodes 76 produces green light having a wavelength of about 5600 Angstroms. An acceptable red diode 74 is a Siemens LDR 1102 light emitting diode, and an acceptable green diode 76 is a Siemens LDG 1153 light emitting diode. The diodes 72 should be matched as to physical shape and output intensity, to produce a beam 62 of uniform intensity along its length. The diodes 72 should be mounted closely together for this same reason.

The light from the diodes 72 enters an optical coupler 78, which produces a bi-chromatic line source from the individual light outputs of the diodes. The optical coupler 78 is made of optical plastic, and has a cylindrical lens 80 at the end adjacent the diodes 72, to efficiently couple the light from the row of diodes 72 into the optical coupler. The other end of the optical coupler 78 has a 45 degree polished surface 82 that acts as a totally internally reflecting surface and reflects the light beam 62 from the diodes 72 through 90 degrees to a ground plastic surface 84. The ground plastic surface 84 diffuses the light and converts the beam 62 from a series of discrete points of light, as produced by the diodes 72, to a generally uniform line source of well mixed light. The beam 62 emerging from the optical coupler 78 need not be a perfectly uniform line source.

The beam 62 passes from the optical coupler 78 to a first polarizer 86, wherein the beam 62 is linearly polarized, as indicated by the arrow 88 of FIG. 2.

The beam 62 then passes through the container 54. The passage of some parts of the line-source beam 62 may be obscured by opaque portions of the container 54, but this effect is taken into account in the manner of analysis of the signals. If the beam is obscured entirely, then no reading is taken and data is gathered from other portions of the container.

After leaving the container 54, the beam 62 passes into the light analyzer assembly 60, illustrated in more detail in FIG. 4. A first portion 90 of the beam 62 passes through a parallel polarizer 92 having a polarization direction parallel to the polarization direction 88 of the first polarizer 86, and enters a first optical detector 94. Similarly, a second portion 96 of the beam 62 passes through a cross polarizer 98 having a polarization direction orthogonal to the polarization direction 88 of the first polarizer 86, and enters a second optical detector 100.

The construction of the two optical detectors 94 and 100 is substantially the same, and the details of detector 94 will be described. After passing through the polarizer 92, the first portion 90 of the beam 62 is focused by a converging lens 102 onto a field lens 104, and thence to a photodiode 106. The lenses 102 and 104 focus the line source beam to a relatively small size to be received by the photodiode 106. The photodiode 106 produces an electrical output signal that is proportional to the intensity of portion of the light beam 62 impinging thereupon. The sensitivity range of the photodiode 106 is sufficiently wide to detect the two different wavelengths of light produced by the diodes 74 and 76.

Figure 5:
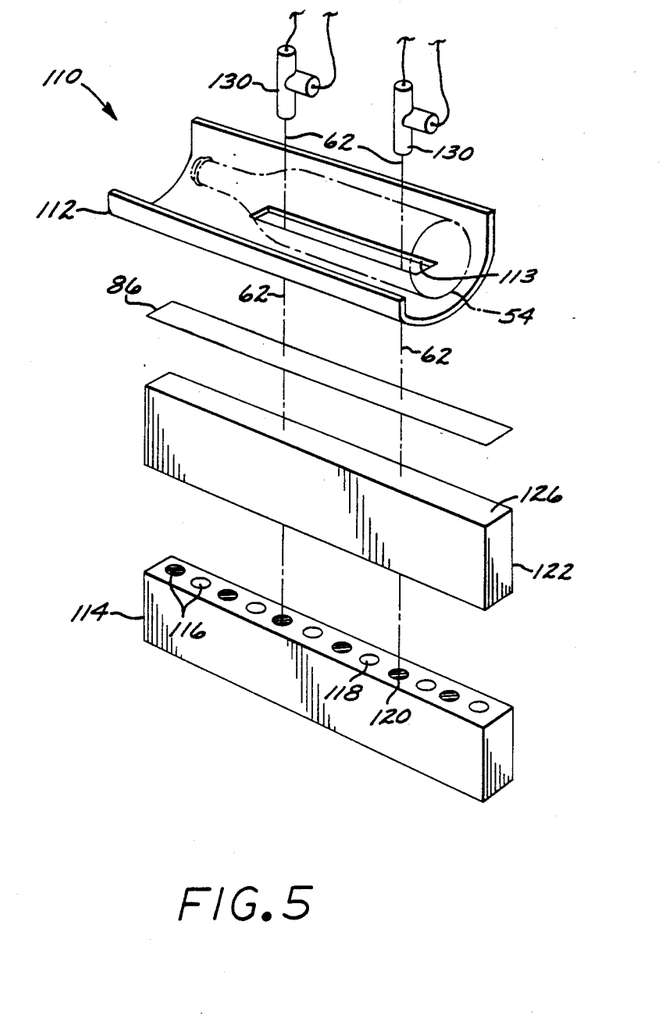
FIG. 5 is perspective diagrammatic view of another embodiment of a measurement apparatus.

Another embodiment of the sorting station 110 is shown in FIG. 5. In this embodiment, the container 54 is supported within a tub 112 having a slot 113 therein, extending along the length of the container 54 to permit light to be passed therethrough. (In yet another approach, the container may be supported on rails to move with its long axis perpendicular to the direction of motion, as distinct from the embodiment of FIG. 2, where the container moves with its long axis parallel to the direction of motion.)

A light source 114, illustrated in FIG. 6, has a long dimension parallel to the axis of the container 54, producing an elongated line beam. The light source 114 produces at least two different wavelengths of light, using at least two types of diodes 116. The two types of diodes 118 and 120 are arranged in alternating fashion along the light source 114. The preferred diodes are a red diode, illustrated as the first diode 118, and a green diode, illustrated as the second diode 120. These diodes are preferably of the type discussed above. (They may also be packaged within a single molded package, as in a Panasonic LN11WP23 unit.) The light from the diodes 118 and 120 enters an optical coupler 122, which has a cylindrical lens 124 adjacent the diodes to maximize the acceptance of light into the coupler. The opposite end of the optical coupler 122 has a ground or etched diffusing surface 126, that alters the light beam 62 from the appearance of a series of point sources to a more uniform line source. The beam 62 enters the first polarizer 86 after it leaves the optical coupler 122.

After passing through the container 54, the beam 62 enters a split beam analyzer 130, illustrated in FIG. 7. The analyzer 130 includes a converging lens 132 that focuses the beam 62 to an optical beam splitter 134. The beam splitter 134, which may be a partially silvered mirror or the like, permits a first portion 136 of about 50 percent of the intensity of the beam to pass through, and reflects a second portion 138 of about 50 percent of the intensity of the beam through an angle of 90 degrees. One of the split beams, here illustrated as the first portion 136, passes through a parallel polarizer 140 having a polarization direction parallel to that of the first polarizer 86 and thence to a first optical detector 142. The other of the split beams, here illustrated as the second portion 138, passes through a cross polarizer 144 having a polarization direction crossed to that of the first polarizer 86 and thence to a second optical detector 146. Each optical detector 142 and 146 produces an output signal related to the intensity of the light impinging thereupon. The split beam analyzer 130 has the advantage over the analyzer illustrated in FIG. 4 of reducing the possibility of error due to different degrees of obscuring of various parts of the beam 62, as due to dirt or labels on the container 54. The light source 114 can be interchanged with the light source 58, and the analyzer 130 can be interchanged with the analyzer 60, where appropriate. The embodiments are described in particular combinations for convenience in illustration.

The diodes in the light emitters are operated in an alternating fashion, and a typical duty cycle is illustrated in FIG. 8. All of the first diodes (emitting a first wavelength of light) are operated for a first period of time P1. Next, all of the second diodes (emitting a second wavelength of light) are operated for a second period of time P2. Finally, the emitter is dark for two periods of time P3 and P4, with no diodes operating. (Alternatively stated, the period in which the emitter is dark is of equal duration to the period in which the first diodes operate plus the time in which the second diodes operate.) The cycle is then repeated. Preferably, each of the four periods is of approximately equal duration. In an operating embodiment, the repetition frequency was 8 kilohertz, but the invention is not so limited.

The alternating operation of the diodes permits a beam of light of the first wavelength to be shone through the container and measured by photodiodes for a period of time. The beam of light of the second wavelength is then shone through the container and measured by the same photodiodes. The ambient light conditions are measured by the photodiodes during the periods that the emitter is dark. In each case, the preferred approach is to utilize an integrated total intensity measured over the appropriate period when the light source is operating or not operating, rather than a peak value or the like. Sampling is accomplished at a high rate, so that the container may be moving past the sorting station as the measurement is taken. A large number of measurements can be taken for each container, and exceptional measurements excluded from consideration by the logic described below. Exceptions can occur because the dirt, obscuring due to labels, and internal reflections within the container, or possibly other reasons. Reference measurements are also taken when no container is present.

The processing aspect of the present invention provides for the analysis of the various transmitted light beams to determine whether the container is optically inactive such as glass or optically active such as certain types of plastic, and the color of the container. The analysis requires a true value of the beam intensity that has been adjusted to account for ambient light conditions, and therefore in each case the corrected beam intensity I is determined by subtracting the measured ambient light intensity from the measured beam produced with the light source operating.

Several types of quantities calculated from the measured data are of use in the analysis. The sum S is the sum of two different corrected beam intensities, and the color index CI, is the difference between two different corrected beam intensities. The total transmitted energy TTE is the sum of the individual sums S for each of the two types of sources, as measured by both detectors. A normalized color index NCI is the quantity obtained by dividing the appropriate color index CI by the appropriate sum S. In each case, average values of quantities can be obtained by averaging several individual computations. Utilizing these defined arithmetic manipulations, a number of different quantities of interest are obtained.

The analysis of the material of construction of a container is performed using the individual sums of corrected beam intensities for parallel and crossed polarizers. Here, $S_p = I_{1p} + I_{2p}$, and $S_c = I_{1c} + I_{2c}$, where subscript p refers to the light measured through the parallel polarizer of the analyzer, the subscript c refers to the light measured through the cross polarizer of the analyzer, the subscript 1 refers to light of the first wavelength, and the subscript 2 refers to light of the second wavelength.

For a material that is not optically active, such as most glasses used in containers, the value of $S_p$ decreases as compared with the value measured when no container is present. For a material that is optically active, such as many plastics including the PET widely used in containers, the value of $S_p$ also decreases as compared with the value measured when no container is present. Thus, $S_p$ cannot be used as the basis for sorting containers, but does provide a check on the presence of containers. For a material that is not optically active, $S_c$ decreases (in proportion to $S_p$) as compared with the value measured when no container is present. For a material that is optically active, $S_c$ increases as compared with the value measured when no container is present (which is nearly zero), because of the rotational effect of the optically active material. The determination of $S_c$ therefore may be used to distinguish between glass and PET plastic by virtue of the polarization characteristics.

The color of the container is assessed through measurement of the total transmitted energy, the color index, and the normalized color index. The total transmitted energy for parallel polarization $TTE_p$ is $TTE_p = I_{1p} + I_{2p}$, the total transmitted energy for cross polarization $TTE_c$ is $TTE_c = I_{1c} + I_{2c}$, the color index for parallel polarization $CI_p$ is $CI_p = CI_{1p} - CI_{2p}$, and the color index for cross polarization $CI_c$ is $CI_c = CI_{1c} - CI_{2c}$.

The normalized color index for parallel polarization $NCI_p$ is $NCI_p = CI_p / TTE_p$, and the normalized color index for cross polarization $NCI_c$ is $NCI_c = CI_c / TTE_c$.

An average total transmitted energy $TTE_a$, for any particular illumination cycle, is $TTE_a = (TTE_p + TTE_c)/2, ps$
the average normalized color index $NCI_a$, for any particular illumination cycle, is $NCI_a = (NCI_p + NCI_c)/2$.

Is preferred that the average values $TTE_a$ and $NCI_a$ be used in making the determinations of color, although acceptable results are obtained using the corresponding parallel or crossed polarizer values.

For a container having a color near to that of the wavelength produced by the first light source, the value of the total transmitted energy is positive, because the light of the first wavelength is strongly transmitted and the light of the second wavelength is strongly attenuated. For a container having a color near to that of the wavelength produced by the second light source, the value of the total transmitted energy is also positive, because the light of the first wavelength is strongly attenuated and the light of the second wavelength is strongly transmitted. For containers of other colors, the total transmitted energy will be positive but smaller, as neither the first nor the second wavelength of light will be strongly transmitted. For a clear container, the total transmitted energy will be positive and greater than for any colored containers, as both wavelengths of light are strongly transmitted. The total transmitted energy therefore provides one measure of the character of the container.

Another measure is provided by the normalized color index, which provides a readily discerned manner of distinguishing between the color of containers. For a container having a color near to the wavelength of the first light source, the normalized color index is large and positive, because the first term is much larger than the second term. For a clear container, the normalized color index is near zero, because both terms are about the same. For a container having a color near to the wavelength of the second source, the normalized color index is large and negative, because the second term is much larger than the first term. The containers of different colors are therefore characterized by the sign of the normalized color index.

As previously noted, as a practical matter most dealers in used containers are primarily interested in sorting as between glass and PET materials of construction, on the one hand, and between red, green, or clear colors on the other. The use of red (about 6650 Angstoms) and green (about 5600 Angstroms) light emitting diodes in the light sources is therefore preferred. The above-discussed principles are, of course, applicable to the use of pairs of modulatable light sources of any two colors. The principles are also applicable on a pairwise basis to sets of three or more diodes where more detailed color-based sorting is required.

The preferred electronic circuitry utilized to perform the calculations and operate the light sources are illustrated in FIGS. 9 and 10. The circuitry for performing calculations for parallel and crossed polarizers is identical, and one exemplary circuit is discussed.

Referring to FIG. 10, the optical detector, such as one of the detectors 94, 100, 142, or 146, which is preferably a photodiode, is connected across the inputs of a high gain amplifier circuit 200. In a preferred form, the amplifier circuit 200 has a 47 kilohm feedback resistor and functions as a transimpedance amplifier. Its output is coupled by means of a coupling capacitor to the input of another operational amplifier 202. Value of its feedback resistor and its input resistor are selected so that the amplifier preferably has a gain of about 10. There is also feedback capacitor, preferably of about 10 picofarads, to perform spike filtering.

The output of the amplifier 202 is AC coupled by a coupling capacitor to the input of another operational amplifier 204. The output of the signal produced on conductor 206 by amplifier 204 represents the AC signal produced by the photodiode and amplified by the amplifiers 200, 202, and 204, which in the preferred embodiment is at 8 kilohertz. The time constants of the AC coupling circuits coupling the amplifiers 200, 202, and 204 are such that any 60 hertz or 120 hertz variations in the signal produced by the photodiode as a result of incandescent or fluorescent ambient light are reduced.

The conductor 206 is connected to the inputs of two multiplex switches 208 and 210 of an electronic multiplexer circuit 212. Electronic multiplexer circuit 212 is preferably a Motorola CD4066 integrated circuit multiplexer. The conductor 206 is also connected to the inputs of two switches 214 and 216 of the multiplexer circuit 212. The circuitry of FIG. 9, in conjunction with the circuitry of FIG. 10, selectively switches the amplified photodiode output signal on conductor 206 to integrating circuits 218 and 220, which will be described in detail after discussing the circuitry for controlling the light emitting diodes.

Referring to FIG. 9, a clock oscillator 222 is implemented by two inverters, a resistor, and a capacitor, whose values are chosen to yield the desired frequency, here 8 kilohertz. The output of the oscillator 222 is provided to the input of a self-clocking flip flop 224, which performs a divide-by-two function. The output of flip flop 224 is connected to the input of another divide-by-two flip flop 226. Both flip flops 224 and 226 are connected to the inputs of logic gating circuitry 228. The outputs of the various gates and inverters and logic circuitry are indicated by the reference letters S1-S8, indicating the corresponding control input signals applied to multiplexer switches 208 and 210 of FIG. 9 to which those logic circuitry outputs are connected in order to determine which of the integrating circuits the amplified output of the photodiode is then being multiplexed.

An inverter 230 of logic circuit 228 generates a pulse that coincides in time with the illumination of the first light source in the timing diagram, FIG. 8. This pulse is supplied to the light emitting diode driver circuit 232 which drives the first source light emitting diodes (that is, the red diodes of the preferred embodiment, such as diodes 74 or 118). Similarly, the output signal of an inverter 234 coincides in time with the illumination of the second light source in the timing diagram. This signal is applied to the input of a second driver circuit 236 that simultaneously drives the light emitting diodes of the second light source, here the green diodes.

The signals S1-S8 are applied to the inputs of the multiplex switches 208 and 210 in the following manner. In operation, during the first time frame of each cycle, the first light source diodes, here the red diodes, are on. Switches 208 and 214 are on, so that the amplified signal on the conductor 206 is fed to the positive input of the differential amplifier 218, which integrates the signal to produce the integrated intensity of the beam as measured by the photodiode, for the first time period. The other input to the differential amplifier 218 is held at ground by switch 211. The signal on the conductor 206 is coupled by the switch 214 to the positive input of a differential amplifier 220, the negative input of which is held at ground by the switch 215. The integrating circuit thus produces a signal which is the integrated intensity of the beam measured by the photodiode for the first time period.

During the period when all the first (red) light sources are off and the second (green) light sources are on, the second time frame of FIG. 8, switches 210 and 214 are closed. The signal on conductor 206, representing the energy being transmitted through the container 54 by the second light source diodes, is coupled to the negative input of an integrating circuit 218 by switch 210, to produce an output signal corresponding to the negative of the integrated intensity of the second light source. The signal on the conductor 206 is simultaneously applied to the positive input of integrating circuit 220 by the closed switch 214. The cumulative effect of the integrating circuit 220 is to add the energies transmitted through the container 54 from the first and second light sources. The cumulative effect of the integrating circuit 218 is to subtract the energy transmitted from the second light source during the second time period from the energy transmitted from the first light source during the first time period. During the third and fourth periods illustrated in FIG. 8, when neither light source is operating, the ambient light level is measured and subtracted from the integrated sum of the first and second periods for both amplifiers 218 and 220. By connecting the ambient light signal on conductor 206 to gates 208 and 210 which are closed alternatively during the third and fourth periods, the integrator 218 removes the ambient background from the color difference signal 240. By connecting the ambient light signal on conductor 206 to gate 216 for the third and fourth periods, integrator 220 removes the ambient background from the total energy signal 241.

The signals produced by the integrating circuits 218 and 220 are supplied to a pair of amplifier circuits 300 and 302, which function as low pass filter amplifiers with offset adjustment resistors 304 and 306. The output signals produced by the low pass filter/amplifier circuits are supplied to two level shift circuits 308 and 310. The color index signal CI is produced on conductor 312 after being amplified and filtered, is applied to an analog-to-digital converter input of a microprocessor 314. The total transmitted energy TTE available at conductor 316 is applied to a second analog-to-digital converter input of the microprocessor 314. The signals CI and TTE for each orientation of polarization are manipulated by the microprocessor in accordance with the procedures set forth above, to determine the material of construction and color of the container. The microprocessor reaches a decision on these matters, and controls the sorting gate 28 to direct the container into the proper crusher and/or bin 30.

In a preferred embodiment, the amplifier 200 is an LF 351 integrated circuit manufactured by National Semiconductor. Amplifiers 202 and 204 are LF 353 integrated circuits, manufactured by National Semiconductor. The amplifiers 218, 230, 220, and 232 are LF 412 integrated circuit differential amplifiers made by National Semiconductor. The level shifters 308 and 310 are LM 336 integrated circuit voltage references manufactured by National Semiconductor. The microprocessor with integral analog-to-digital converter is an M50734 integrated circuit manufactured by Mitsubishi Electric.

The system described hereinabove has been constructed and used to correctly measure the color index of containers and to distinguish between PET and glass containers. It provides a clear signal to sort containers on these bases.

Thus, the present approach provides an apparatus and process for distinguishing and sorting transparent and partially transparent containers by material of construction and color, without the need for human intervention. No bar code or similar reference is required for sorting. Although particular embodiments of the invention have been described in detail for purposes of illustration, various modifications may be made without departing from the spirit and scope of the invention. Accordingly, the invention is not to be limited except as by the appended claims.

What is claimed is:

1. Apparatus for analyzing the character of a light transmitting container, comprising:
    a container support adapted for supporting a container;
    a first source of beam of polarized light of a first wavelength disposed to direct the beam of polarized light through the container supported in the container support;
    a second source of a beam of polarized light of a second wavelength disposed to direct the beam of polarized light through the container supported in the container support;
    a first light analyzer having
        a parallel polarizer relative to the polarization of the light from the first source, the parallel polarizer being disposed to intercept a first portion of the beam from the first source of polarized light after the beam has passed through the container,
        a cross polarizer relative to the polarization of the light from the first source, the cross polarizer being disposed to intercept a second portion of the beam from the first source of polarized light after the beam has passed through the container,
        a first detector that measures the intensity of a light beam, the first detector being disposed to detect the first portion of the beam from the first source, after the beam has passed through the parallel polarizer, and
        a second detector that measures the intensity of a light beam, the second detector being disposed to detect the second portion of the beam from the first source, after the beam has passed through the cross polarizer;
    a second light analyzer having
        a parallel polarizer relative to the polarization of the light from the second source, the parallel polarizer being disposed to intercept a first portion of the beam from the second source of polarized light after the beam has passed through the container,
        a cross polarizer relative to the polarization of the light from the second source, the cross polarizer being disposed to intercept a second portion of the beam from the second source of polarized light after the beam has passed through the container,
        a first detector that measures the intensity of a light beam, the first detector being disposed to detect the first portion of the beam from the second source, after the beam has passed through the parallel polarizer, and
        a second detector that measures the intensity of a light beam, the second detector being disposed to detect the second portion of the beam from the second source, after the beam has passed through the cross polarizer;
    means for analyzing the character of the container using the intensities measured by the first light analyzer and the second light analyzer.

2. The apparatus of claim 1, where the means for analyzing includes
    means for determining the sum of the intensities measured by the first detector of the first light analyzer and the first detector of the second light analyzer.

3. The apparatus of claim 1, where the means for analyzing includes
    means for determining the difference of the intensities measured by the first detector of the first light analyzer and the first detector of the second light analyzer.

4. The apparatus of claim 1, wherein the first light source and the second light source are disposed so that the beams of light produced by the first light source and the second light source are coincident, and further including
    a beam controller that controls the operation of the first light source and the second light source to operate in an alternating fashion.

5. The apparatus of claim 4, wherein the first light analyzer and the second light analyzer are included within a single light analyzer, and further including
    a light analyzer controller that controls the operation of the light analyzer so that it performs the functions of the first light analyzer when the beam controller operates the first light source, and performs the functions of the second light analyzer when the beam controller operates the second light source.

6. Apparatus for analyzing the character of a light transmitting container, comprising:
   a container support adapted for supporting a container;
   a first source of a beam of light of a first wavelength disposed to direct the beam of light through the container supported in the container support;
   a second source of a beam of light of a second wavelength disposed to direct the beam of light through the container supported in the container support, the first source and the second source being disposed so that the beam of light of the first wavelength and the beam of light of the second wavelength are at least in part parallel and coincident on a beam path;
   a first polarizer disposed in the beam path at a location prior to passage of the beams through the container;
   a beam controller that controls the operation of the first light source and the second light source to operate in an alternating fashion.
   a light analyzer having
      a parallel polarizer relative to the polarization of the light from the first polarizer, the parallel polarizer being disposed to intercept a first portion of the beam path at a location after the beams have passed through the container,
      a cross polarizer relative to the polarization of the light from the first polarizer, the cross polarizer being disposed to intercept a second portion of the beam path at a location after the beams have passed through the container,
      a first detector that measures the intensity of a light beam, the first detector being disposed to detect the light passing through the parallel polarizer, and
      a second detector that measures the intensity of a light beam, the second detector being disposed to detect the light passing through the cross polarizer; and
   means for analyzing the character of the container using the intensities measured by the light analyzer.

7. The apparatus of claim 6, wherein the means for analyzing includes
   means for determining the sum of the intensities measured by the first detector when the first light source operates and the first detector when the second light source operates.

8. The apparatus of claim 6, wherein the means for analyzing includes
   means for determining the difference of the intensities measured by the first detector when the first light source operates and the second detector when the first light source operates.

9. The apparatus of claim 6, wherein the means for analyzing includes
   means for determining the sum of the intensities measured by the first detector when the first light source operates and the first detector when the second light source operates; and
   means for determining the difference of the intensities measured by the first detector when the first light source operates and the second detector when the first light source operates.

10. The apparatus of claim 6, wherein the light produced by the first source is red.

11. The apparatus of claim 6, wherein the light produced by the second source is green.

12. Apparatus for determining whether a container is formed of glass or an optically active plastic, comprising:
   a container support adapted for supporting a container of an unknown, but optically transmissive material;
   a source of a beam of light disposed to direct the beam of light through the container supported in the container support;
   a first polarizer disposed in the beam path at a location prior to passage of the beam through the container;
   a light analyzer having
      a parallel polarizer relative to the polarization of the light from the first polarizer, the parallel polizer being disposed to intercept a first portion of the beam at a location after the beam has passed through the container,
      a cross polarizer relative to the polarization of the light from the first polarizer, the cross polarizer being disposed to intercept a second portion of the beam at a location after the beam has passed through the container,
      a first detector that measures the intensity of a light beam, the first detector being disposed to detect the light passing through the parallel polarizer, and
      a second detector that measures the intensity of a light beam, the second detector being disposed to detect the light passing through the cross polarizer; and
   means for determining the difference of the intensity measured by the first detector and the intensity measured by the second detector.

13. Apparatus for determining the color of a container that is transmissive to light, comprising:
   a container support adapted for supporting a container;
   a first source of a beam of light of a first wavelength disposed to direct the beam of light through the container supported in the container support;
   a second source of a beam of light of a second wavelength disposed to direct the beam of light through the container supported in the container support;
   a first light analyzer having
      a first detector that measures the intensity of a light beam, the first detector being disposed to detect the intensity of the beam from the first source, after the beam has passed through the container, and
      a second detector that measures the intensity of a light beam, the second detector being disposed to detect the intensity of the beam from the second source, after the beam has passed through the container; and
   means for determining the difference of the intensities measured by the first detector and the second detector.

14. Apparatus for determining the color of a container that is transmissive to light, comprising:
   a container support adapted for supporting a container;

a first source of a beam of light of a first wavelength disposed to direct the beam of light through the container supported in the container support;

a second source of a beam of light of a second wavelength disposed to direct the beam of light through the container supported in the container support, the first source and the second source being disposed so that the beam of light of the first wavelength and the beam of light of the second wavelength are at least in part parallel and coincident on a beam path;

a beam controller that controls the operation of the first light source and the second light source to operate in an alternating fashion;

a light analyzer having a detector that measures the intensity of a light beam, the detector being disposed to detect the intensity of the coincident beam; and means for determining the difference of the intensity measured by the detector when the first source is operating and the intensity measured by the detector when the second source is operating.

15. A process for determining whether a container is formed of glass or an optically active plastic, comprising the steps of:

finding a polarization difference index for the container, utilizing the steps of passing a beam of polarized light through a container, passing a portion of the beam through a parallel polarizer, after it has passed through the container, passing another portion of the beam through a cross polarizer, after it has passed through the container, and determining the polarization difference index as the difference in intensity of the portion of the beam passed through the parallel polarizer and the intensity of the portion of the beam passed through the cross polarizer;

repeating the step of finding with no container present; and comparing the polarization difference index determined with a container present and with no container present.

16. A process for determining the color components of a container that is at least partly transparent to light, comprising the steps of:

transmitting a beam of light through the container, the beam having at least two different wavelengths therein;

measuring the intensity of the transmitted beam at the two different wavelengths; and calculating a normalized color index of the container as the difference between the intensities of the beam at the two different wavelengths divided by the sum of the intensities of the beam at the two different wavelengths.

17. A process for characterizing the nature of a container that is at least partially transparent to light, comprising the steps of:

transmitting the beam of light through the container, the beam having at least two different wavelengths therein;

measuring the intensity of the transmitted beam at the two different wavelengths;

calculating a color index of the container as the difference between the intensities of the beam at the two different wavelengths.

finding a polarization difference index for the container, utilizing the steps of passing a beam of polarized light through a container, passing a portion of the beam through a parallel polarizer, after it has passed through the container, passing another portion of the beam through a cross polarizer, after it has passed through the container, and determining the polarization difference index as the difference in intensity of the portion of the beam passed through the parallel polarizer and the intensity of the portion of the beam passed through the cross polarizer;

repeating the step of finding with no container present; and comparing the polarization difference index determined with a container present and with no container present.

* * * * *